(12) United States Patent
Gonzalez

(10) Patent No.: US 11,202,846 B2
(45) Date of Patent: Dec. 21, 2021

(54) DIFFUSER WITH DIFFERENT TEMPERATURE RESPONSE

(71) Applicant: Santos Oscar Gonzalez, Edinburg, TX (US)

(72) Inventor: Santos Oscar Gonzalez, Edinburg, TX (US)

( * ) Notice: Subject to any disclaimer, the term of this patent is extended or adjusted under 35 U.S.C. 154(b) by 0 days.

(21) Appl. No.: 17/165,052

(22) Filed: Feb. 2, 2021

(65) Prior Publication Data
US 2021/0236679 A1    Aug. 5, 2021

Related U.S. Application Data

(60) Provisional application No. 62/995,552, filed on Feb. 4, 2020.

(51) Int. Cl.
| *A61L 9/03* | (2006.01) |
| *A61L 2/26* | (2006.01) |
| *A61L 2/20* | (2006.01) |
| *A47K 1/09* | (2006.01) |

(52) U.S. Cl.
CPC ................... *A61L 9/03* (2013.01); *A47K 1/09* (2013.01); *A61L 2/20* (2013.01); *A61L 2/26* (2013.01); *A61L 2202/11* (2013.01); *A61L 2202/121* (2013.01); *A61L 2202/122* (2013.01); *A61L 2209/133* (2013.01); *A61L 2209/135* (2013.01)

(58) Field of Classification Search
CPC ..... A61L 2/20; A61L 2/26; A61L 9/02; A61L 9/03; A61L 9/032; A61L 9/035; A61L 2202/11; A61L 2202/121; A61L 2202/122; A61L 2209/133; A61L 2209/135
See application file for complete search history.

(56) References Cited

U.S. PATENT DOCUMENTS

| 941,200 | A | 11/1909 | Jones |
| 1,212,335 | A | 1/1917 | Feinberg |
| 1,501,835 | A | 7/1924 | Bash |
| 1,951,585 | A | 4/1934 | Tomson |
| 2,180,213 | A | 11/1939 | Peake |
| 2,280,431 | A | 4/1942 | Hart |
| 2,468,733 | A | 5/1949 | Boulicault |
| 3,367,610 | A | 2/1968 | Linquist |
| 3,794,181 | A | 2/1974 | Conham |
| 3,884,635 | A | 5/1975 | Sloan |
| 5,295,575 | A | 3/1994 | Gonzalez |
| 6,004,516 | A | 12/1999 | Rasouli |
| 7,132,084 | B1 | 11/2006 | Rasoli |
| 7,179,436 | B2 | 2/2007 | Willis |
| 7,691,336 | B2 | 4/2010 | Westring |
| 8,721,962 | B2 | 5/2014 | Woo |
| 9,399,079 | B2 | 7/2016 | McMinn |
| 10,471,223 | B2 * | 11/2019 | Bourque ............... G16H 40/63 |
| 2004/0033182 | A1 | 2/2004 | Duffy |
| 2006/0029518 | A1 | 2/2006 | Yu |
| 2014/0339070 | A1 | 11/2014 | Visioni |

* cited by examiner

*Primary Examiner* — Timothy C Cleveland
(74) *Attorney, Agent, or Firm* — G. Turner Moller

(57) ABSTRACT

A diffuser includes an adjustable heater having a temperature control knob providing indicia coordinated with like indicia on packets of vaporizable materials of different tendencies to vaporize. By manipulating the temperature control knob to the indicia corresponding to the indicia on the packet, a suitable quantity of energy is delivered to the diffuser resulting in suitable vaporization. One indicia is color coded packets and similarly color coded markings adjacent the temperature control knob.

19 Claims, 4 Drawing Sheets

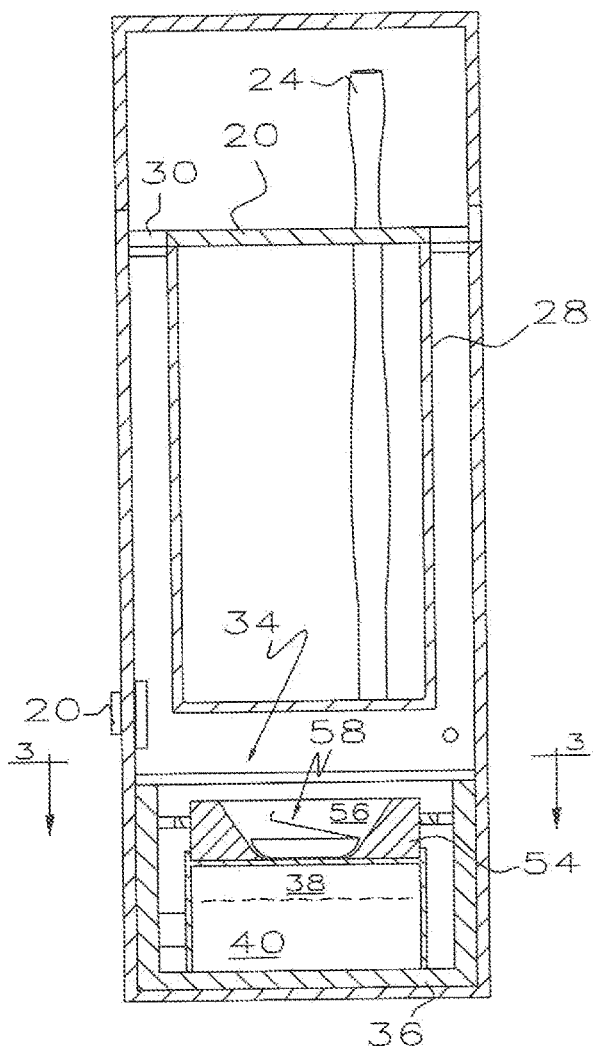
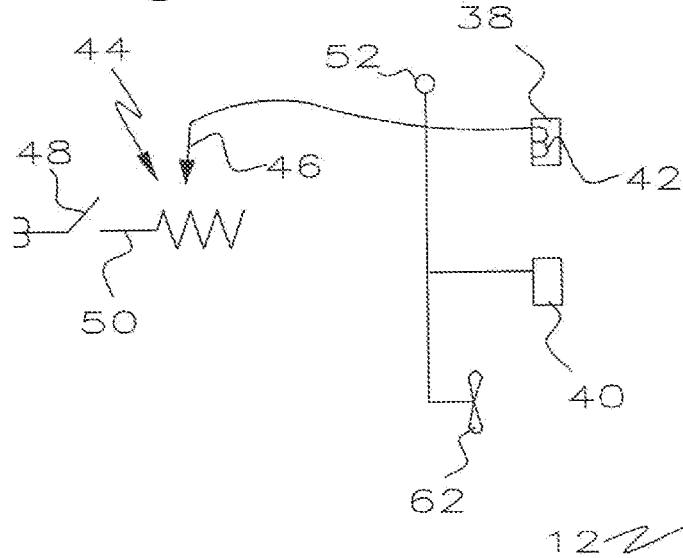
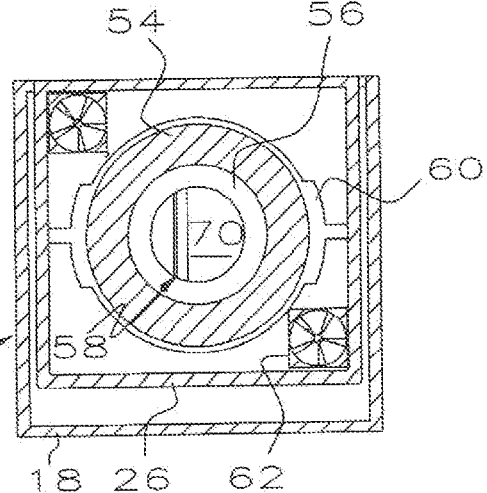

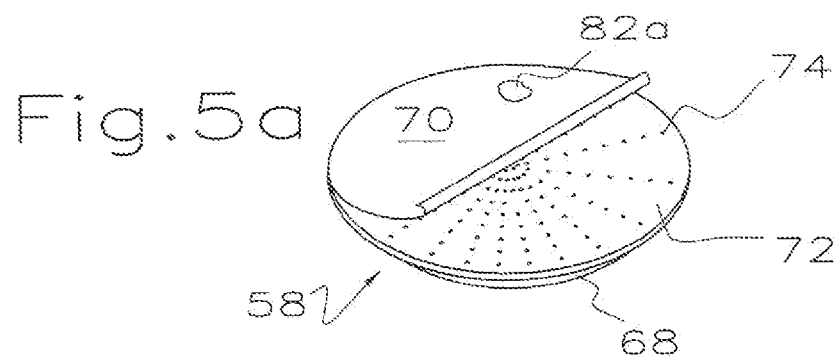
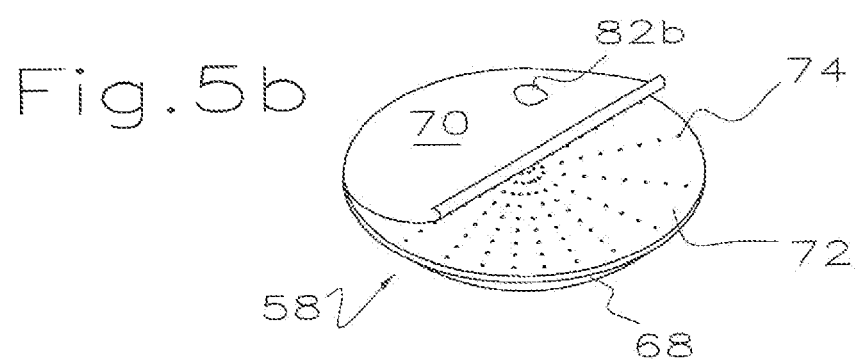
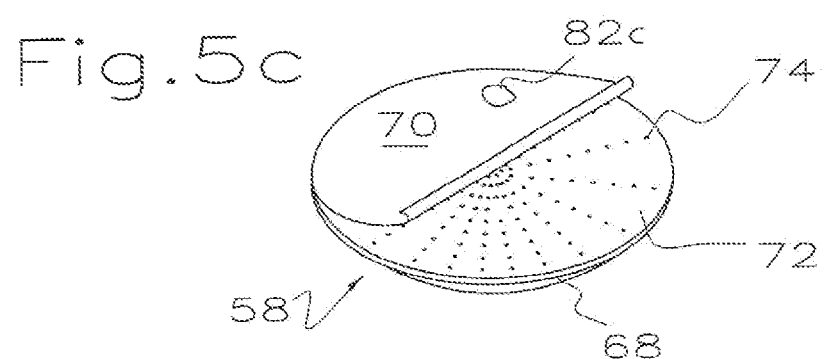
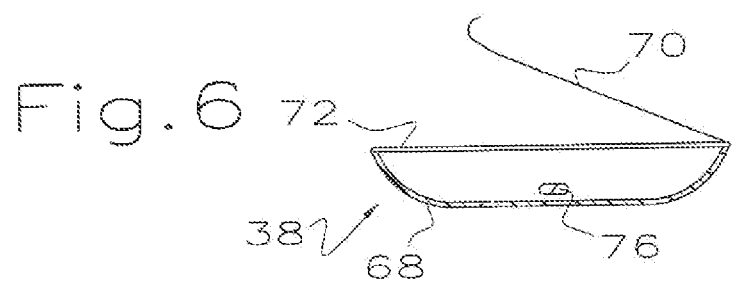

DIFFUSER WITH DIFFERENT TEMPERATURE RESPONSE

This application claims priority of Provisional Patent Application 62/995,552 filed Feb. 4, 2020, the subject matter of which is wholly incorporated herein by reference.

This invention relates to a diffuser for evaporating one of a series of substances of different inclination to vaporize.

BACKGROUND OF THE INVENTION

This invention relates to a diffuser for partially evaporating a series of substances that have different inclinations to vaporize. One use of such a device is in providing essential oil vapors where the oils have different boiling points and distributing the vapors as desired. One particular use of such a device is in a toothbrush holder where toothbrushes are exposed to the vapors in order to freshen or sanitize toothbrushes.

Toothbrush holders and electrically heated diffusers are well known in the prior art as shown in U.S. Pat. Nos. 941,200; 1,212,335; 1,501,835; 1,951,585; 2,180,213; 2,280,431; 2,468,733; 3,367,610; 3,794,181; 3,884,635; 5,295,575; 6,004,516; 7,132,084; 7,179,436 7,691,336 8,721,962 9,399,079; CA2429445; CN2201384436; IN201741030085; JP200426806; WO2011021980; WO2013050011 and U.S. Printed Patent Applications 2004033182; 20060029518 and 20140339070.

SUMMARY OF THE INVENTION

This invention is an improvement over the device shown in U.S. Pat. No. 5,295,575.

There is disclosed an electrically heated diffuser having a temperature control device including a series of indicia representative of the different vaporization tendencies of several vaporizable liquids. The user may select the indicia which corresponds to a similar indicia on a packet of material to be vaporized and thereby actuate the heater to produce a desired vaporization of the material.

There is also disclosed a series of packets of vaporizable materials having different indicia representing the vaporizable tendency of the material contained therein. The indicia on the packet corresponds to the indicia on the diffuser so the user may readily set the diffuser to perform satisfactorily with the material in the packet. In a preferred embodiment, the indicia on the diffuser is a series of different colors and the packets are colored in the same series of different colors so the temperature supplied by the diffuser is matched to the vaporization tendency of the material in the packet.

The diffuser may be incorporated into a toothbrush holder so the vaporized materials freshen or disinfect the exposed toothbrushes. In the alternative, the diffuser may simply allow the vaporized material to escape into the room or area where it is located to provide a pleasing aroma or be part of an air conditioning system. One set of materials used in the diffuser may be that class of compounds known as essential oils.

The crux of the invention may be an electrically heated diffuser having a temperature control device including a series of indicia representative of different vaporization tendencies of vaporizable liquids used with the device. The user may select the indicia which corresponds to an indicia on a packet of material to be vaporized and thereby actuate the heater to produce a desired vaporization of the material. In some embodiments, a magnetic stirrer may be provided in the packet and/or electrically operated fans may be inside the diffuser housing to promote delivery of vapors from the packet.

It is an object of this invention to provide an improved method and apparatus for diffusing vaporizable materials.

Another object of this invention is to provide an improved device for creating pleasant vapors.

A more specific object of this invention is to provide a combination toothbrush holder and diffuser to generate freshening or disinfecting vapors to toothbrushes.

These and other objects and advantages of this invention will become more apparent as this description proceeds, reference being made to the accompanying drawings and appended claims.

BRIEF DESCRIPTION OF THE DRAWINGS

FIG. 2 is a vertical cross-sectional view of the device of FIG. 1;

FIG. 3 is a horizontal cross-sectional view of the device of FIG. 1;

FIG. 4 is a schematic view of the operating devices in the diffuser of FIG. 1;

FIGS. 5a, 5b and 5c are isometric views of a series of containers having therein different vaporizable materials and an indicia which is indicative of the vaporizable tendency of the material therein;

FIG. 6 is a cross-sectional view of the container of FIGS. 5a, 5b, 5c;

DETAILED DESCRIPTION

Figure 1:
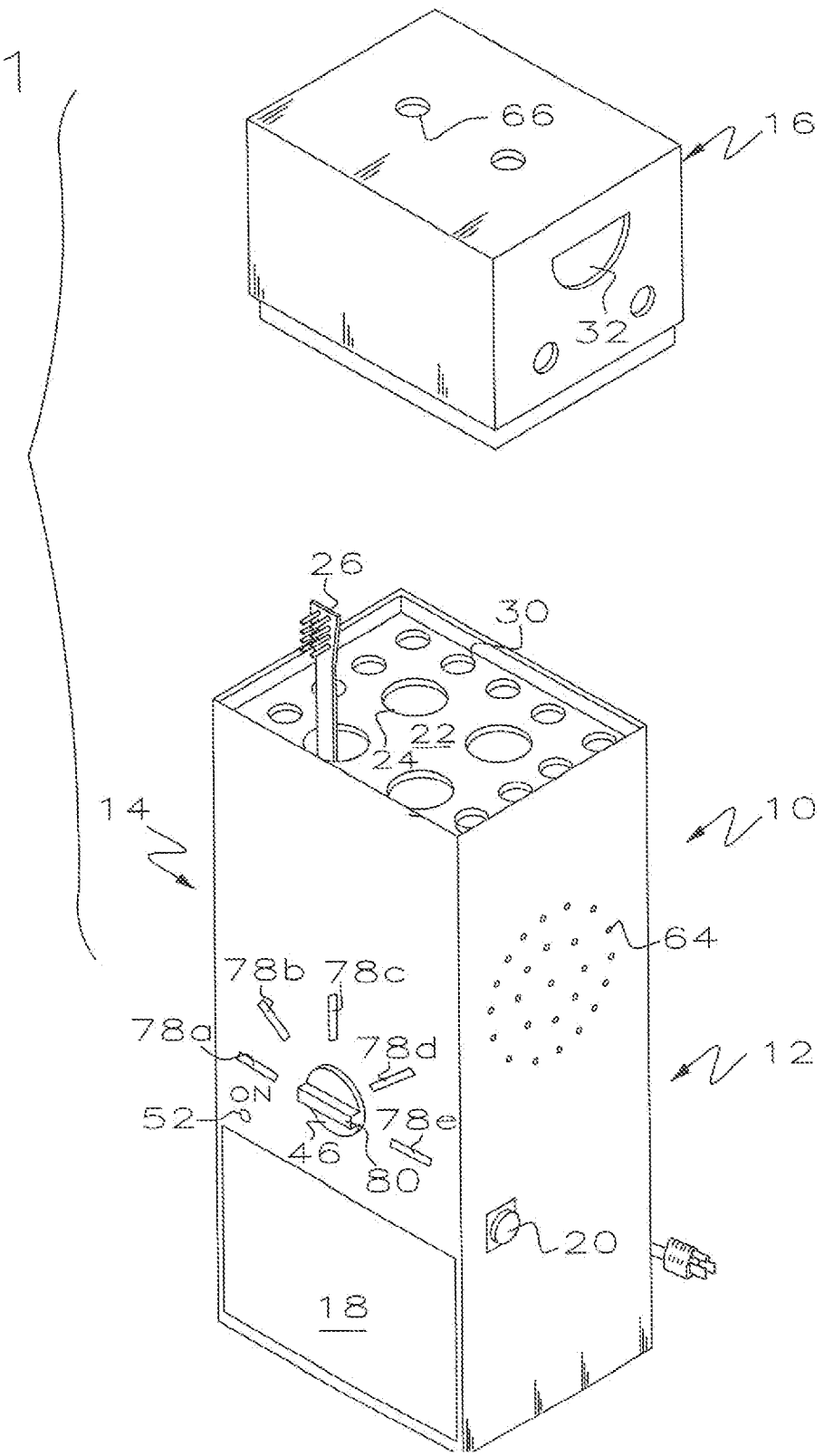
FIG. 1 is an exploded isometric view of a diffuser of this invention, illustrated as incorporated into a toothbrush holder.

Referring to FIGS. 1-6, a toothbrush holder 10 includes a housing 12 of any suitable configuration having a base 14 and a lid 16. The base 14 provides a drawer or door 18 movable between open and closed positions to provide access to the interior of the housing 12. A suitable latch (not shown) may be provided to hold the door 18 in the closed position. A release mechanism 20 may be provided to operate the latch and allow the drawer or door 18 to open. The interior of the base 14 includes a toothbrush holding platform or partition 22 having openings 24 for receiving one or more toothbrushes 26. The toothbrushes 26 are supported in any suitable fashion, as by the provision of a receptacle 28 depending from the platform 22. As explained more fully hereinafter, passages 30 in the platform 22 allow vapors to contact bristles on the toothbrush and thereby freshen and disinfect the toothbrush 26. The lid 16 may be of any suitable type and is illustrated as being of transparent plastic having suitable grasping recesses 32.

The base 14 houses a heating assembly 34 including a receptacle 36 receiving an electrically operated heater 38 including a magnetic field generator 40 to produce a rotating magnetic field for rotating a magnetizable stirrer as more fully pointed out hereinafter. The heater 38 also includes a electric heating element 42 and a temperature control system 44 including a temperature control device or knob 46 accessible from the exterior of the housing 12. A switch 48 is provided in a connection 50 to a source of power in order to turn the heating assembly 34 on and off and a light or other suitable device 52 may be provided to provide an indication to the user that the device is on.

The heating assembly 34 includes a thermally insulating cup or dish 54 having a recess 56 for receiving a packet 58 of a vaporizable material as more fully explained hereinafter. The cup 54 is in heat exchanging relation with the heater 38 and may preferably be supported thereby. A pair of brackets 60 may be provided to center the cup 54 on the heater 38. In some embodiments, the heating assembly 34 may include a fan 62 to circulate vapors emanating from the packet 58 throughout the housing 12. In other embodiments, vapor flow is induced by heat supplied from the heating assembly 34.

An important advantage of the holder 10 is to provide a flow path for vapors produced by material in the packet 58. In some embodiments, vapor may exit the housing 12 through one or more arrays of openings 64 in one or multiple sides of the housing base 14. In other embodiments, vapor may exit the housing 12 through openings 66 in the lid 16. This has the advantage of minimizing condensation of the essential oil in the housing 12. In other embodiments, vapor may exit the housing through both sets of openings 64, 66.

The packets 58 may be of any suitable type and include a container 68 for the vaporizable material and a lid 70 sealing the contents inside the container 68. The lid 70 conveniently is a peelable flexible material adhesively adhering to the container 68 or to an intermediate wall 72 having perforations 74 therein. The intermediate wall 72 may be more-or-less rigid to provide a support for the peelable lid 70 and minimize spillage of liquids in the container 68 while allowing vapors to escape. A magnetic rod 76 may be placed in the liquid material in the container 68 to stir the liquid in response to the rotating magnetic field produced by the generator 40.

An important advantage of the diffuser 10 is the manner in which the temperature control system 44 and manually positioned control element 46 are used to provide an appropriate temperature for the vaporizable material in the packet 58. A series of indicia 78a-78e are provided on the housing base 14 adjacent the path of movement of the control element 46 which includes a pointer or reference mark 80 so that when the knob 46 is turned to align the reference mark 80 with a selected one of the indicia, a desired amount of energy is delivered to the heating assembly 34, the magnetic generator 40 and the fans 62.

The indicia 78 are different from each other in a manner that corresponds to a parameter of material in the packets 58. The parameter is a physical characteristic of the liquid material in the packet that correlates to, or is predictive of, the tendency of the liquid material to vaporize. The selected parameter may differ with different materials in the packet 58. Most volatile scent producing materials are flammable so this may be taken into account when selecting a parameter. The parameter may be boiling point in an inert gas, the temperature at which the material begins smoking when heated in air, density, viscosity or the like.

Each packet 58 also incudes different indicia 82a-82e that correlate to, or is identical to, one of the indicia 78a-78e. In other words, the indicia 78, 82 cooperate to match the power supplied to the heating assembly 34 with the material in the packet 58. The indicia 78, 82 may vary widely and include a patch of color, numbers, symbols, diagrams and the like. It may be preferred to use color for a variety of reasons, e.g. simplicity of use and instruction, pleasing packaging where the entire lid 70 may be of the desired color, and the like.

Although many different types of vaporizable materials may be used in the diffuser 10, what may be a preferred type is known as essential oils. An essential oil is an essence of plant material of which there are hundreds of examples. The raw plant material is generally pressed to produce a liquid which is then filtered and purified to produce a volatile mixture of compounds, which produce desired scented or disinfectant vapors. Typical plants used in the manufactur of essential oils are flowers, coconut, jojoba, almonds, olives, basil, cinnamon, sassafras, vetiver, ginger, fennel, anise, citrus epicaps, peppermint and the like.

Because of the large number of compounds in an essential oil and because of their relative presence, essential oils inherently have different rates of vaporization and thus differently vaporize at room temperature. By differentially warming, adjusting stirring speeds and adjusting fan speed, different essential oils or mixtures of essential oils may produce more desirable effects when compared to heating all essential oils to the same temperature. It will be apparent that different essential oils or different mixtures of essential oils may vaporize differently in response to more heat, higher stirring speeds or more air circulation. Thus, the power supplied to the heater 38, magnetic generator 40 and/or fans 62 may be adjusted independently of each other to provide optimum vaporizing conditions. These *desiderata* produce some difficulty to teach a user to operate the diffuser 10 in a more-or-less optimum manner.

Many commercially available essential oils are mixtures containing compounds of differing vaporizing tendency. If a diffuser has only one operating temperature, mixtures are made so their vaporizing tendency corresponds to the single operating temperature. With the ability to provide different operating conditions, i.e. temperature, stirring speed and/or fan speed, and correlate the operating temperature with mixtures of different vaporizing tendencies, many more essential oil mixtures may be formulated and used successfully.

Operation of the diffuser 10 should now be apparent. The user opens the drawer 18 and places a desired packet 58 in the recess 56 of the dish 54. The user turns the knob 46 of the temperature control system 44 so the pointer 80 aligns with the indicia 78 corresponding to the indicia 82 on the packet 58. If color is being used as indicia, the user turns the knob 46 of the temperature control system 44 so the pointer 80 aligns with the indicia 78 that is the same color as the indicia on the selected packet 58. The user closes the drawer 18 and plugs the connection 50 into a suitable source of electrical power and turns the switch 48 on. The heater 38 delivers a desired amount of energy to the element 42 and magnetic field generator 40 to simultaneously warm the liquid material in the dish 54 and rotate the magnetic rod/stir bar 76 to stir material in the packet 58 thereby deliver vapors upwardly in the housing 12, either by fan induced draft or from thermal draft, depending on use of the variable speed of the fans 62. Vapors flow upwardly in the housing 12 and exit through one or both of the array of openings 64, 66, depending on the details of construction of the housing 12. Vapors flowing past the toothbrush 26 freshen and/or disinfect bristles on the toothbrush in accordance with the nature and quantity of the vapors.

Figure 7:
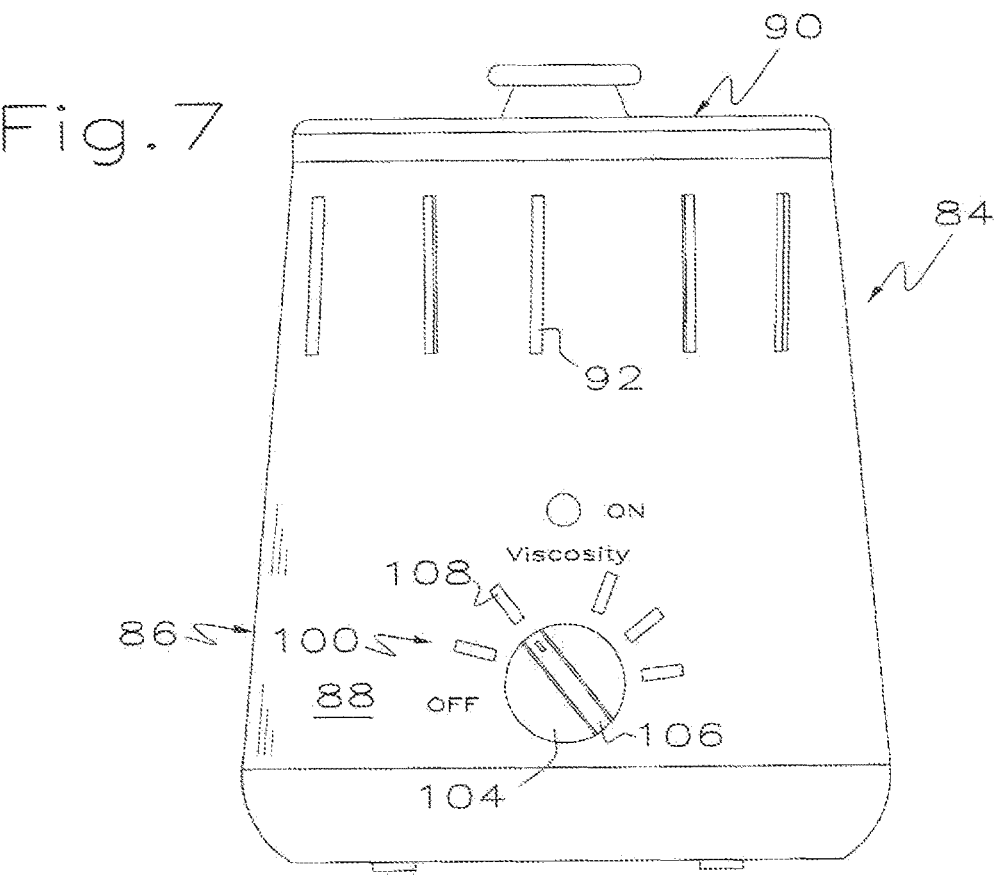
FIG. 7 is a front view of a diffuser configured to deliver a vaporizable material into the area of the diffuser.
Figure 8:
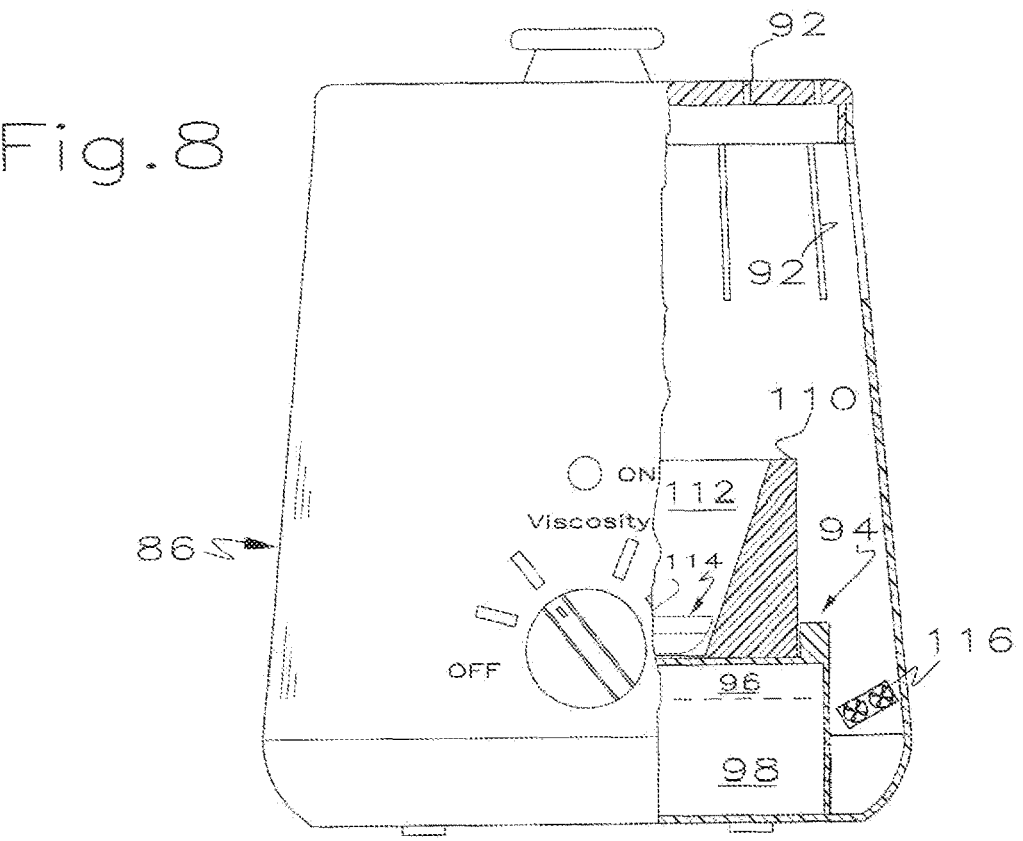
FIG. 8 is a partial front view, partly cross-sectional view of the diffuser of FIG. 7.

Referring to FIGS. 7-8 there is illustrated a diffuser 84 which operates on the same principles as the diffuser 10. The diffuser 84 may be located in a room to be infused with vapors from the device or incorporated into an air conditioning system to deliver vapors throughout the facility being heated or cooled by the system. The diffuser 84 includes a housing 86 of any suitable configuration having a base 88 and a lid 90. The housing 86 provides a compartment receiving operating of the diffuser and provides a series of openings 92 distributing vapors to the area around the diffuser 84. The housing 86 and lid 90 may be made of any suitable material such as polymer plastics, ceramics or the like.

Inside the housing 86 is a heater assembly 94 including a heater 96 and a magnetic field generator 98. The heater assembly 94 includes a temperature control system 100 for adjusting the amount of energy delivered to the heater 96. The control system 100 includes a manually operated temperature control element such as a rotatable knob 104 having a pointer or mark 106. Arrayed in the path of movement of the knob 104 are a series of indicia 108 functioning the same as the indicia 78 of the diffuser 10. A heat tolerant dish 110 includes a recess 112 receiving a packet 114 of vaporizable material. The packet 114 may be the same as the packet 58 and include indicia representing a series of values of a parameter correlated with the tendency of material in the packet 58 to vaporize. It will be seen that operation of the diffuser 84 is essentially the same as the diffuser 10 so that manipulating the knob 104 to position the pointer 106 to align with a selected one of the indicia 108 delivers an amount of energy to the heater 96, the magnetic generator 40 and the fan 116 that is appropriate considering the vaporizing tendency of material in the packet 114.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. In combination,
a diffuser including a housing having a holder configured to support at least one toothbrush having bristles and an assembly including an electrically operated heater and a temperature control system configured to adjust energy delivered to the heater, the temperature control system including a series of indicia and a user controlled element movable relative to the series of different indicia to adjust energy to the heater depending on the location of the movable element relative to the series of different indicia; and
a packet of vaporizable material, the material in the packet being of a group of materials having different vaporizing tendencies, the packet including an indicia representing the vaporizing tendency of material in the packet, indicia on the packets corresponding to the indicia of the temperature control system, the packets being configured to be received in heat exchange relation with the heater;
the combination being configured to deliver an appropriate amount of energy to the heater when the temperature control element aligns with the temperature control indicia corresponding to the indicia on the packet;
the housing being configured to direct vapors from the packet onto bristles of the toothbrush.

2. The combination of claim 1 further comprising a series of similar packets having therein a series of materials of different vaporizing tendency, the packets of the series of packets each having a different indicia corresponding to the vaporizing tendency of material therein.

3. The combination of claim 1 wherein the indicia of the temperature control system comprises a series of colored marks in a path of movement of the temperature control element and the indicia on the packets comprises patches of the same series of colors.

4. The combination of claim 3 wherein the different indicia correlate to different values of a parameter affecting a vaporizing tendency of material in the packet.

5. The combination of claim 3 wherein the temperature control indicia and packet indicia represent a series of values of the same vaporizing tendency parameter.

6. The combination of claim 1 wherein the vaporizing tendency being selected from the group consisting essentially of a boiling point of liquid material in the packet taken in an inert atmosphere, a temperature in air where the liquid material begins to smoke, density of the liquid material in the packet and viscosity of the liquid material in the packet.

7. The combination of claim 1 wherein the packets each comprises a cup configured to hold a liquid and a lid configured to be peeled off of the container, the lid having an upper surface, the upper surface being of the lid being entirely of a color, the color being the indicia of the packet.

8. The combination of claim 1 wherein the housing includes at least one opening configured to deliver vapors from the packet to an exterior of the housing.

9. A method of using a diffuser having a housing having a holder configured to support at least one toothbrush having bristles and an assembly including an electrically operated heater and a temperature control system configured to adjust energy delivered to the heater, the temperature control system including a series of indicia and a user controlled element movable relative to the series of different indicia to adjust energy to the heater depending on the location of the movable element relative to the series of different indicia; and a packet of vaporizable material, the material in the packet being of a group of materials having different vaporizing tendencies, the packet including an indicia representing the vaporizing tendency of material in the packet, indicia on the packets corresponding to the indicia of the temperature control system, the packet being configured to be received in heat exchange relation with the heater; the combination being configured to deliver an appropriate amount of energy to the heater when the temperature control element aligns with the temperature control indicia corresponding to the indicia on the packet, the method comprising the steps of:
placing the packet in heat exchange relation with the heater;
moving the user controlled element in alignment with a temperature control indicia corresponding to the packet indicia;
delivering electricity to the heater, warming the packet and delivering vapors out of the diffuser; and
directing vapors from the packet onto bristles of the toothbrush.

10. The method of claim 9 wherein the assembly includes a generator of a rotating magnetic field and a fan configured to circulate vapors through the housing and wherein the packet includes a magnetic stir rod and the delivering step comprising simultaneously delivering electricity to the magnetic generator and fan and thereby simultaneously stirring liquid in the packet and circulating vapors through the housing.

11. The method of claim 9 further comprising a series of second packets having therein a series of materials of different vaporizing tendency, the packets of the series of packets each having a different indicia corresponding to the vaporizing tendency of material therein, and the method further comprises placing one of the second packets in heat exchange relation with the heater;

moving the user controlled element in alignment with the temperature control system indicia that corresponds to the indicia on the one of the second packets; and delivering electricity to the heater, warming the one of the second packets and delivering vapors out of the diffuser.

12. The method of claim 9 wherein the indicia of the temperature control system comprises a series of colored marks in a path of movement of the temperature control element and the indicia on the packet comprises patches of the same colors as the temperature control system colored marks and the moving step comprises aligning the user controlled element with the temperature control system colored mark that corresponds to the color on the packet placed in heat exchange relation with the heater.

13. The method of claim 9 wherein the packet comprises a cup configured to hold a liquid and a lid configured to be peeled off of the container, the lid having an upper surface, the upper surface being of the lid being entirely of a color, the color being the indicia of the packet and the moving step comprises aligning the user controlled element with the colored mark that corresponds to the color on the packet placed in heat exchange relation with the heater.

14. The method of claim 9 wherein the housing includes at least one opening communicating with an exterior of the housing and the method comprising delivering vapors from the packets through the opening to the exterior of the housing.

15. In combination, a diffuser including a housing having a holder configured to support at least one toothbrush having bristles and at least one opening communicating with an exterior of the housing; and an assembly including an electrically operated heater and a temperature control system configured to adjust energy delivered to the heater;

the housing being configured to receive a packet of vaporizable material, the material in the packet being of a group of materials having different vaporizing tendencies, the packet including an indicia representing the vaporizing tendency of material in the packet, the packets being configured to be received in heat exchange relation with the heater;

the assembly being configured to deliver an appropriate amount of energy to the heater in accordance with the indicia on the packet;

the housing being configured to direct vapors from the packet onto bristles of the toothbrush and through the opening toward an exterior of the housing.

16. The combination of claim 15 comprising a series of similar packets having therein a series of materials of different vaporizing tendency, the packets of the series of packets each having a different indicia corresponding to the vaporizing tendency of material therein.

17. The combination of claim 16 wherein the packets each comprises a cup configured to hold a liquid and a lid configured to be peeled off of the container, the lid having an upper surface, the upper surface being of the lid being entirely of a color, the color being the indicia of the packet.

18. The combination of claim 16 wherein the temperature control system includes a manually moveable temperature control element and a series of colored marks in a path of movement of the temperature control element and the indicia on the packets comprises patches of the same series of colors.

19. The combination of claim 18 wherein the different indicia correlate to different values of a parameter affecting a vaporizing tendency of material in the packet.

* * * * *